United States Patent [19]

Kobayashi

[11] Patent Number: 4,470,300
[45] Date of Patent: Sep. 11, 1984

[54] APPARATUS FOR AND METHOD OF DETERMINING A CAPACITANCE

[75] Inventor: Hiroshi Kobayashi, Yokohama, Japan

[73] Assignee: Nissan Motor Company, Limited, Kanagawa, Japan

[21] Appl. No.: 367,223

[22] Filed: Apr. 9, 1982

[30] Foreign Application Priority Data

Apr. 10, 1981 [JP] Japan ................................ 56-53101

[51] Int. Cl.³ .............................................. G01F 23/26
[52] U.S. Cl. ................................. 73/304 C; 73/61.1 R; 324/61 QS
[58] Field of Search ................... 73/304 C, 61.1 R; 324/61 QS; 331/65

[56] References Cited

U.S. PATENT DOCUMENTS

| 3,213,439 | 10/1965 | Atkinson | |
| 3,684,952 | 8/1972 | Lundstrom | 324/61 QS |
| 4,083,248 | 4/1978 | Maier | 73/304 C |
| 4,259,865 | 4/1981 | Myers | 73/304 C |
| 4,296,472 | 10/1981 | Sarkis | 73/304 C |

FOREIGN PATENT DOCUMENTS

| 1103275 | 2/1968 | United Kingdom . |
| 1232675 | 5/1971 | United Kingdom . |
| 1523338 | 8/1978 | United Kingdom . |
| 2059506A | 9/1980 | United Kingdom . |
| 2064136A | 10/1980 | United Kingdom . |
| 2055477 | 3/1981 | United Kingdom . |
| 2081452A | 7/1981 | United Kingdom . |

OTHER PUBLICATIONS

Graze: "Elektrische Messung nichtelektrischen Grössen", (1962), pp. 260–266.

Primary Examiner—Stephen A. Kreitman
Assistant Examiner—John E. Chapman, Jr.
Attorney, Agent, or Firm—Lowe, King, Price & Becker

[57] ABSTRACT

An apparatus for determining a capacitance includes a capacitor, an oscillator, and a detector. The capacitor is partially immersed in liquid containing gasoline and alcohol in such a manner that the liquid may enter the capacitor, whereby the capacitance of the capacitor varies with the level of the liquid. The oscillator is connected to the capacitor and generates a oscillatory signal which depends on the capacitance of the capacitor and the frequency of which is set higher than a reference value dependent on the alcohol concentration in the liquid. The detector is connected to the oscillator and measures the capacitance of the capacitor according to the oscillatory signal of the oscillator to determine the level of the liquid.

7 Claims, 9 Drawing Figures

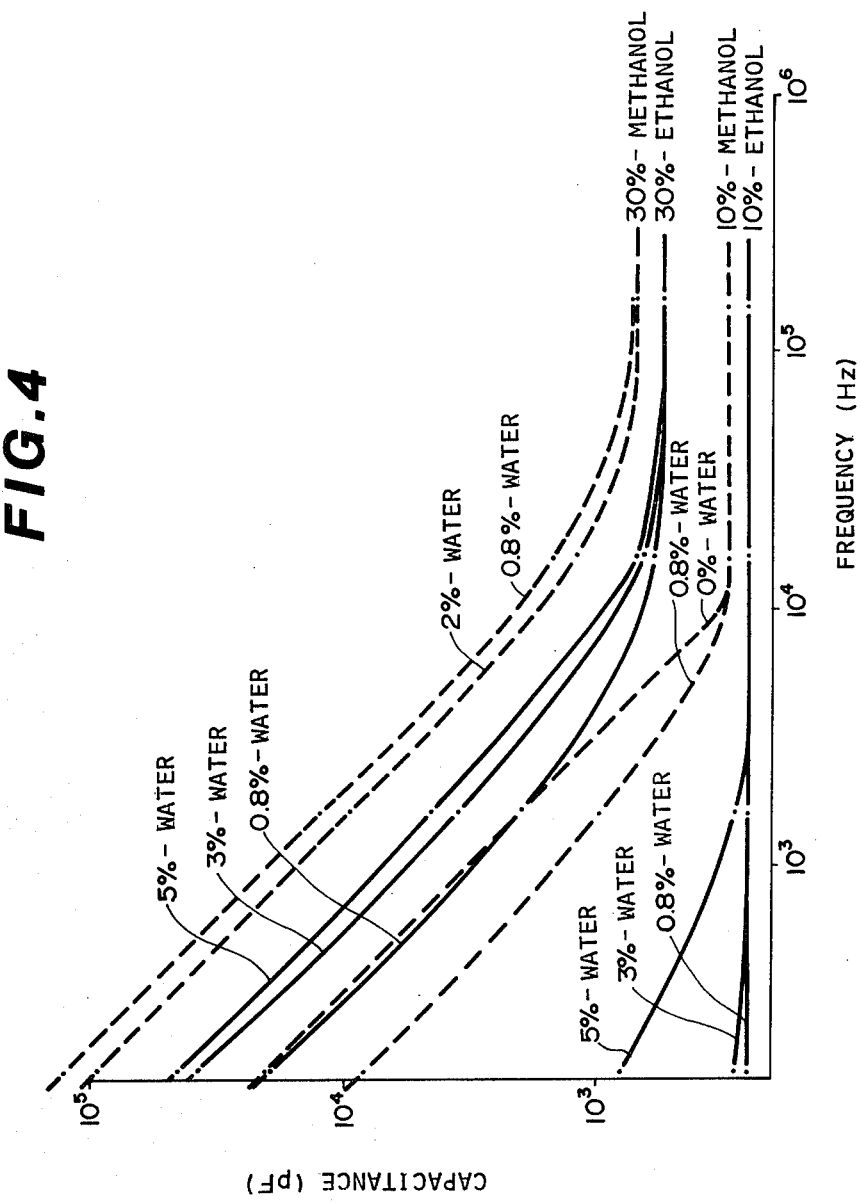

AMOUNT OF FUEL REMANINING

APPARATUS FOR AND METHOD OF DETERMINING A CAPACITANCE

BACKGROUND OF THE INVENTION

1. Field of the Invention

This invention relates to an apparatus for and method of determining a capacitance which is adapted to gauge the level of a liquid or gauge the concentration of liquid mixture constituent.

2. Description of the Prior Art

It is well-known to utilize a capacitor to measure the level of liquid. In this case, the capacitor is partially immersed in the liquid so that its capacitance varies with the level of liquid. The capacitance is measured to determine the liquid level. However, such a conventional gauge of the capacitance type has difficulty in measuring the level of gasoline-based fuel containing alcohol, called "gasohol".

SUMMARY OF THE INVENTION

It is an object of the present invention to provide an apparatus for and method of determining the value of a capacitance which is adapted to accurately measure the level of a gasoline/alcohol mixture, that is, gasohol.

Another object of the present invention is to provide an apparatus for and method of determining a capacitance which is adapted to measure the alcohol concentration of gasohol.

In accordance with the present invention, an apparatus for and method of determining a capacitance includes a capacitor, an oscillator, and a detector. The capacitor is partially immersed in liquid containing gasoline and alcohol in such a manner that the liquid may enter the capacitor, whereby the capacitance of the capacitor varies with the level of the liquid. The oscillator is connected to the capacitor and generates an oscillatory signal having a frequency which depends on the capacitance of the capacitor and the frequency of which is set higher than a reference value dependent on the alcohol concentration in the liquid. The detector is connected to the oscillator and measures the capacitance of the capacitor according to the period of the oscillatory signal of the oscillator to determine the level of the liquid.

The above and other objects, features and advantages of the present invention will be apparent from the following description of preferred and alternative embodiments thereof, taken in conjunction with the drawings.

BRIEF DESCRIPTION OF THE DRAWINGS

FIG. 4 is a graph of experimental measurements of the capacitance of the capacitor in FIGS. 1 to 3 at selected frequencies of the pulses from the oscillator in FIGS. 1 to 3 while the fuel tank in FIG. 1 holds a fixed amount of different several gasohols, most of which include some water;

DETAILED DESCRIPTION OF THE PREFERRED EMBODIMENTS

Figure 1:
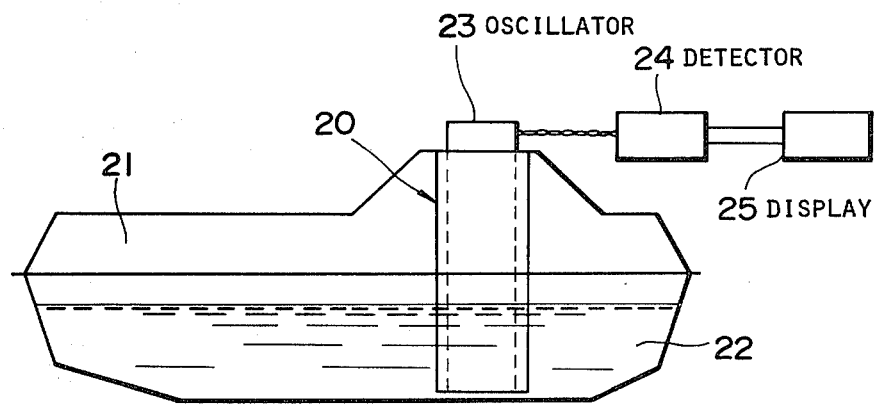
FIG. 1 is a diagrammatic view, partly in cross-section, of a fuel level gauge according to a first embodiment of the present invention.
Figure 2:
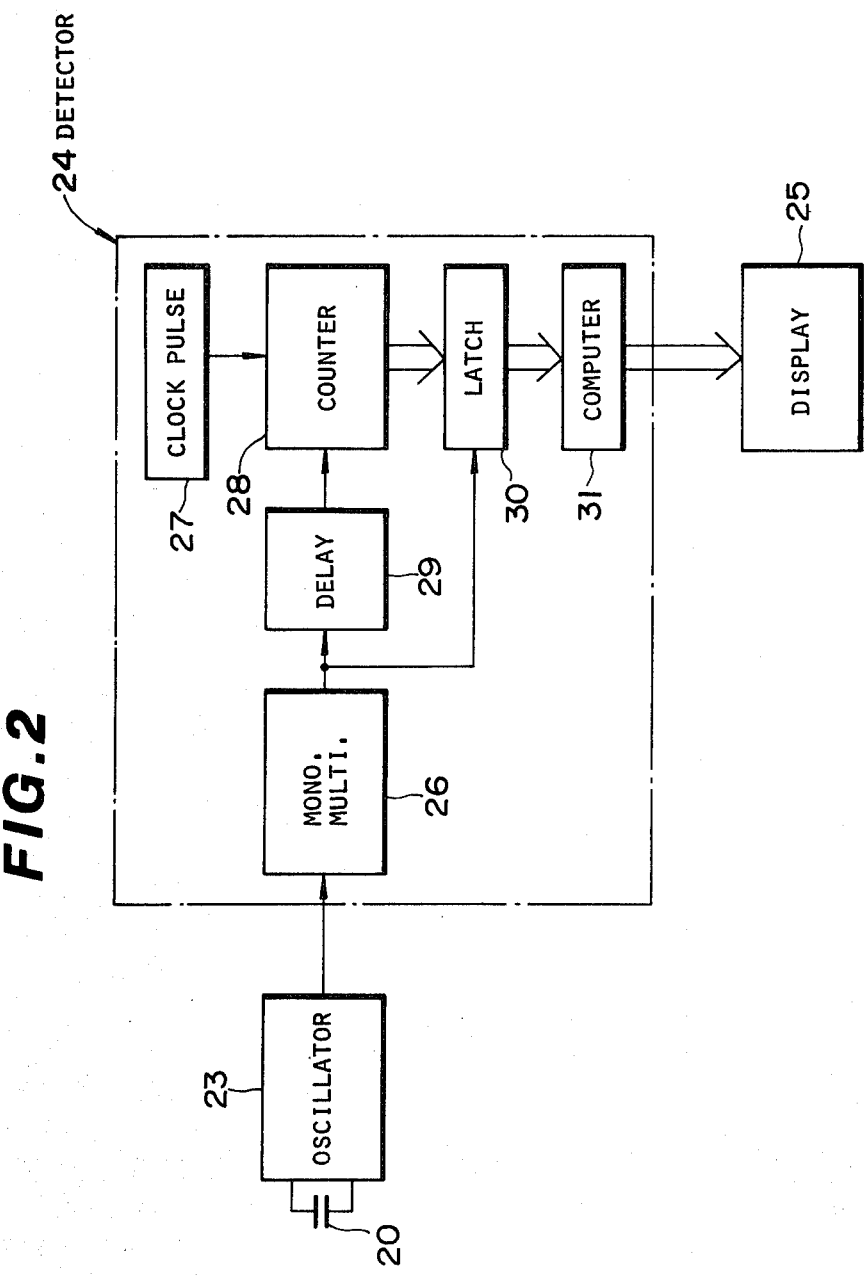
FIG. 2 is a schematic diagram of the fuel level gauge in FIG. 1.

With reference to FIGS. 1 and 2, there is shown a fuel level gauge according to a first embodiment of the present invention. The gauge includes a capacitor 20 which is disposed within a fuel tank 21 containing liquid fuel 22, such as gasohol. The capacitor 20 includes a pair of concentric tubular conductive members spaced a predetermined distance apart. The axis of the capacitor 20 is vertical, and extends from the bottom to the top of the fuel tank 21. The fuel 22 enters the gap between the members of the capacitor 20, so that the capacitance of the capacitor 20 varies with the level of fuel 22 due to the considerable difference in dielectric constant between fuel and air.

An oscillator 23 is mounted on the top of the fuel tank 21. The oscillator 23 is connected to the capacitor 20 so as to generate a signal which oscillates at a frequency depending on the capacitance of the capacitor 20. A period detector 24 is connected to the oscillator 23 in order to detect the period of the oscillatory signal therefrom. The period detector 24 thus generates a signal which depends on and represents the period of the oscillatory signal from the oscillator 23. A display 25 is connected to the period detector 24 to receive and indicate the signal representative of the period of the oscillatory signal of the oscillator 23. Since the capacitance of the capacitor 20 depends on the level of the fuel 22, the frequency or period of the oscillatory signal of the oscillator 23 varies with the level of fuel 22, so that the display 25 indicates the level of fuel 22. The display 25 can directly indicate the amount of fuel remaining in the tank 21, provided that the capacitor 20, the fuel tank 21, and the oscillator 23 are arranged so as to linearize the relation between the period of the oscillatory signal of the oscillator 23 and the amount of fuel remaining in the tank 21.

The oscillator 123 includes an astable multivibrator. To ensure the dependence of the frequency or period of the oscillatory signal on the capacitance of the capacitor 20, the capacitor 20 is connected to the astable multivibrator 23 in such a manner as to constitute an oscillating capacitance factor of the oscillating circuit in the astable multivibrator 23. The frequency or period of the pulse train from the astable multivibrator 23 thus depends on the capacitance of the capacitor 20.

Figure 3:
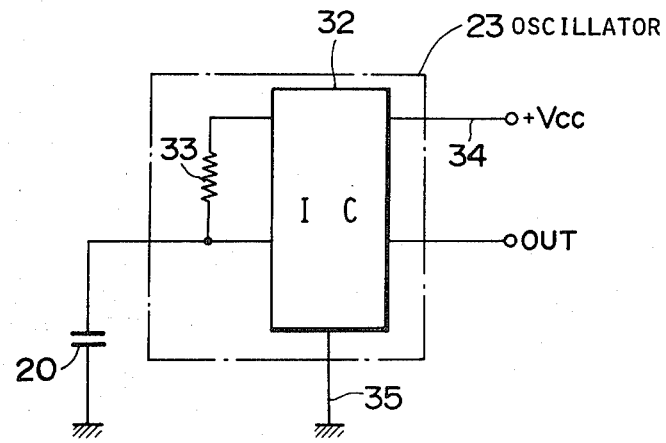
FIG. 3 is a schematic diagram of the oscillator in FIGS. 1 and 2.

As illustrated in FIG. 3, the oscillator 23 is composed of a commercially available IC chip 32 designed as a monostable multivibrator and a resistor 33 connected to the IC chip 32. For example, the IC chip 32 can be "ICM 7555" made by Internics Co., U.S. The capacitor 20 is connected to the IC chip 32, which is connected to a dc power source (not shown) by way of a power supply line 34 and a grounding line 35 so as to be powered. The capacitor 20, the IC chip 32, and the resistor 33 constitute a well-known astable multivibrator which oscillates at a frequency or period depending on the capacitance of the capacitor 20 and the resistance of the resistor 33. The upper limit of the oscillation of this astable multivibrator in frequency ranges several tens of KHz to 100 KHz.

Returning to FIGS. 1 and 2, the period detector 24 includes a monostable multivibrator 26, which is connected to the oscillator 23 to receive the pulse train from the oscillator 23. The monostable multivibrator 26 converts each pulse from the oscillator 23 into an extremely short pulse. In the period detector 24, a clock pulse generator 27 derives pulses at a fixed frequency much higher than that of the oscillatory signal of the oscillator 23, and a counter 28 is connected to the clock 27 to receive and count the fixed-frequency pulses from the clock 27. The monostable multivibrator 26 is connected to the counter 28 by way of a delay circuit 29 to supply the short pulses to the counter 28 as reset pulses for the count action. Thus, the counter 26 is repeatedly reset at time intervals equal to the periods of the oscillatory signal of the oscillator 23. The period detector also includes a latch circuit 30, which is connected to the counter 28 to read and hold the counted pulse number in the counter 28. The monostable multivibrator 26 is connected to the latch circuit 30 to supply the short pulses to the latch circuit 30 as control or strobe pulses for the latch action. Thus, the latch circuit 30 reads and holds the counted pulse number in response to a short pulse from the monostable multivibrator 26. The delay circuit 29 causes the counter 28 to be reset immediately after the latch circuit 30 reads and holds the counted pulse number in the counter 28. Therefore, the counter 28 counts for fixed-frequency pulses for a time equal to the period of the oscillatory signal of the oscillator 23, and the latch circuit 30 reads and holds the number of the fixed-frequency pulses which the counter 28 receives for a time equal to the period of the oscillatory signal of the oscillator 23. In this way, the period detector 24 measures the period of the oscillatory signal of the oscillator 23 by use of the clock pulses and holds the measured result in the latch circuit 30. The period detector further includes a programmable microcomputer or microprocessor 31, which is connected to the latch circuit 30 to receive the data held in the latch circuit 30. The microcomputer 31 calculates and determines the amount of fuel remaining in the tank 21 in a well-known unit system, such as liters (l), on the basis of the received data indicative of the period of the oscillatory signal of the oscillator 23. The microcomputer 31 carries out a calculation according to a program which is preliminarily stored in the microcomputer 31 and is determined in view of the relation between the period of the oscillatory signal of the oscillator 23 and the amount of fuel remaining in the tank 21. In the case where the period of the oscillatory signal of the oscillator 23 has a strictly-linear relation with the amount of fuel remaining in the tank 21, the microcomputer program can be just a proportional calculation or multiplication and thus a proportional calculator or multiplier may be employed instead of the microcomputer 31.

The display 25 consists of a set of seven segment LED (light-emitting diode) displays, which are connected to the microcomputer 31 to receive and indicate the determined result of the amount of fuel remaining in the tank 21.

Gasohol often contains a small amount of water. The water content in gasohol has a sensitive influence on the measured value of the period of the pulses from the oscillator 23 and thus the value of the capacitance of the capacitor 20. FIG. 4 is a plot of the results of experimental measurements of the capacitance of the capacitor 20 at selected frequencies of the pulses from the oscillator 23 while the fuel tank 21 holds a fixed amount of gasohol containing 10%-ethanol, 30%-ethanol, 10%-methanol, or 30%-methanol and 0%, 0.8%, 2%, 3%, or 5%-water. The experimental results reveal that the influence of the water content in gasohol on the measured value of the capacitance of the capacitor 20 decreases as the frequency of the pulses from the oscillator 23 increases. The lower limits of the frequencies of the pulses from the oscillator 23 wherein there is a negligibly small influence of the water content in gasohol on the measured value of the capacitance of the capacitor 20, are 3 KHz, 80 KHz, 15 KHz, and 150 KHz respectively for gasohols containing 10%-ethanol, 30%-ethanol, 10%-methanol, and 30%-methanol respectively; each of these frequencies is at a point where the curve in FIG. 4 makes a transition from horizontal to partially horizontal and partially vertical.

In view of the above experimental results, an important feature of this embodiment is as follows: The capacitor 20 and the oscillator 23 including the resistor 33 are so arranged that the oscillator 23 generates pulses at frequencies having a minimum value which is higher than a predetermined reference value depending on the alcohol concentration in gasohol and the kind of the alcohol in gasohol. For example, the predetermined values are preferably preset to 3 KHz, 80 KHz, 15 KHz, and 150 KHz respectively for gasohols containing 10%-ethanol, 30%-ethanol, 10%-methanol, and 30%-methanol respectively. The frequency of the pulses from the oscillator 23 is minimized when the fuel tank 21 is full. Therefore, to meet the requirement of the lower limit of the frequency, the resistance of the resistor 33 is usually so chosen that the frequency of the pulses from the oscillator 23 is above the predetermined reference value when the fuel tank 21 is full. Furthermore, the predetermined reference value for the frequency of the pulses from the oscillator 23 is preferably 50 KHz, and most preferably 90 KHz for gasohol containing 85%-gasoline and 15%-methanol.

Figure 5:
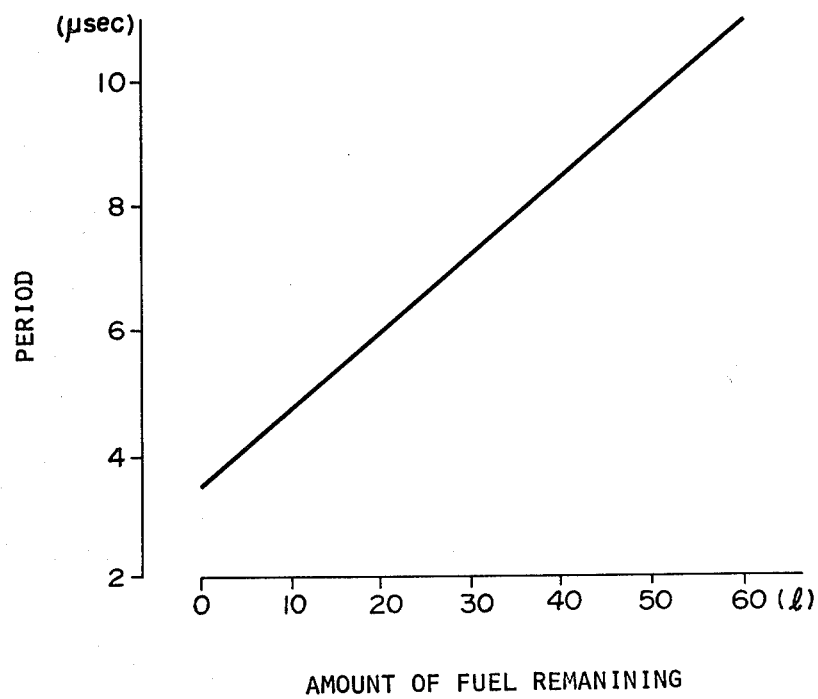
FIG. 5 is a graph of the relation between the period of the oscillatory signal of the oscillator in FIGS. 1 to 3 and the amount of fuel remaining in the tank in FIG. 1.

FIG. 5 is a graph of an example of a linear or proportional relation between the amount of fuel remaining in the tank 21 and the period of the pulses from the oscillator 23. In this case, the fuel employed is gasohol containing 85%-gasoline and 15%-methanol and the minimum frequency of the pulses from the oscillator 23 is set to about 90 KHz.

Figure 6:
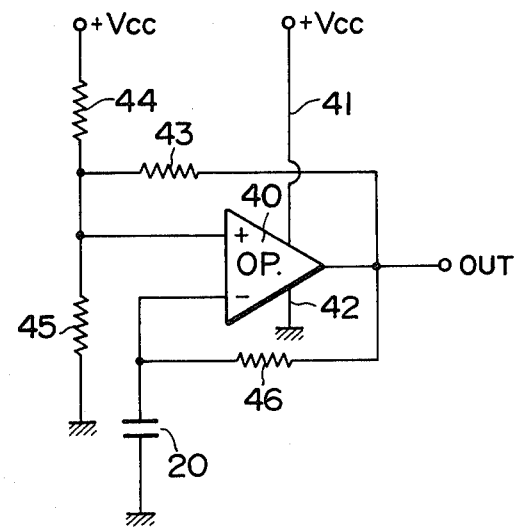
FIG. 6 is a schematic diagram of an oscillator according to a first alternative embodiment of the present invention.

FIG. 6 is a schematic diagram of a first alternative embodiment of an oscillator 23, which includes an operational amplifier 40, such as "CA3100" made by RCA Co. The amplifier 40 is connected to a dc power source (not shown) by way of a power supply line 41 and a grounding line 42 so as to be powered. The output terminal and the positive input terminal of the amplifier 40 are connected by way of a resistor 43. The positive input terminal of the amplifier 40 is connected to the positive terminal of the dc power source by way of a resistor 44, and is grounded by way of a resistor 45. The output terminal and the negative input terminal of the amplifier 40 are connected by way of a resistor 46. One terminal of the capacitor 20 is connected to the negative input terminal of the amplifier 40, and the other terminal thereof is grounded. The operational amplifier 40, the resistors 43, 44, 45, and 46, and the capacitor 20 constitute an astable multivibrator which generates pulses at a frequency depending on the resistance of the resistor 46 and the capacitance of the capacitance 20. This astable multivibrator can generate pulses at a frequency up to 200-300 KHz. The output terminal of the amplifier 40 is connected to the monostable multivibrator 26 of the period detector 24 to supply the latter with the pulse train, the frequency of which depends on the capacitance of the capacitor 20.

Figure 7:
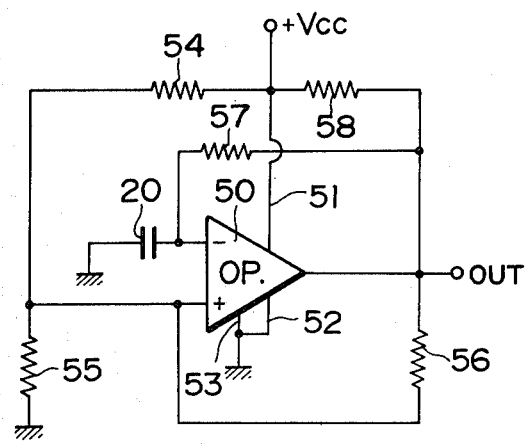
FIG. 7 is a schematic diagram of an oscillator according to a second alternative embodiment of the present invention.

FIG. 7 is a schematic diagram of a second alternative embodiment of an oscillator 23, which includes an operational amplifier 50, such as "LM311" made by National Semiconductor Co. The amplifier 50 is connected to a dc power source (not shown) by way of a power supply line 51, grounding lines 52 and 53 so as to be powered. The positive input terminal of the amplifier 50 is connected to the positive terminal of the dc power source by way of a resistor 54, and is grounded by way of a resistor 55. The positive input terminal and the output terminal of the amplifier 50 are connected by way of a resistor 56. The negative input terminal and the output terminal of the amplifier 50 are connected by way of a resistor 57. The output terminal of the amplifier 50 is connected to the positive terminal of the dc power source by way of a resistor 58. One terminal of the capacitor 20 is connected to the negative input terminal of the amplifier 50, and the other terminal thereof is grounded. The operational amplifier 50, the resistor 54, 55, 56, 57 and 58, and the capacitor 20 constitute an astable multivibrator which generates pulses at a frequency depending on the resistance of the resistor 57 and the capacitance of the capacitor 20. This astable multivibrator can generate pulses at a frequency up to 500 KKz. The output terminal of the amplifier 50 is connected to the monostable multivibrator 26 of the period detector 54 to supply the latter with the pulse train, the frequency of which depends on the capacitance of the capacitor 20.

A reference capacitor (not shown) may be provided in a position, such as in a fuel supply line or at the bottom of the fuel tank 21, always immersed in fuel. In this case, the dielectric constant of fuel is measured by use of the reference capacitor. The measured indication of the period of the oscillatory signal from the oscillator 23 and thus that of the capacitance of the capacitor 20 is corrected in response to the measured value of the dielectric constant of fuel to more accurately determine the amount of fuel remaining in the tank 21. The above correction ensures accurate determination of the amount of fuel remaining in the tank 21 even when changes in the dielectric constant of fuel result from unanticipated factors, such as changes in the composition of fuel, the presence of foreign substances, or changes in temperature.

Figure 8:
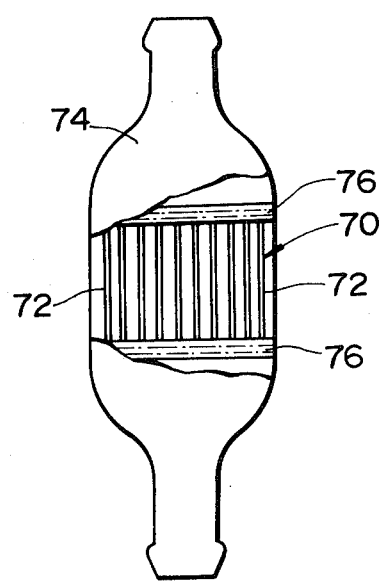
FIG. 8 is a side elevational view, with portions broken away, of a chamber including a capacitor in an apparatus for measuring the alcohol concentration in fuel according to a second embodiment of the present invention.

FIG. 8 is a diagram of an apparatus according to a second embodiment of the present invention, which is directed to a gauge for measuring the alcohol concentration in fuel, such as gasohol. The gauge includes a capacitor 70 which consists of conductive plates 72 evenly spaced within a chamber 74 filled with fuel. Fuel fills the gaps in the capacitor 70. Fixed insulating seats 76 hold the upper and lower ends of the plates 72 to secure the capacitor 70. The chamber 74 including the capacitor 70 is disposed in a fuel supply line so as to be continually immersed in the fuel. In the case of gasohol since the relative dielectric constant of gasoline considerably differs from that of alcohol, the relative dielectric constant of gasohol varies with the alcohol concentration in the gasohol. Thus, the capacitance of the capacitor 70 also varies with the alcohol concentration due to the dependence thereof on the dielectric constant of gasohol within the capacitor 70. All of the capacitor 70 is immersed in the fuel, so that the capacitance of the capacitor 70 depends strictly on the dielectric constant of the fuel. As a result, the measurement of the capacitance of the capacitor 70 determines the dielectric constant of gasohol and thus the alcohol concentration is gasohol.

Figure 9:
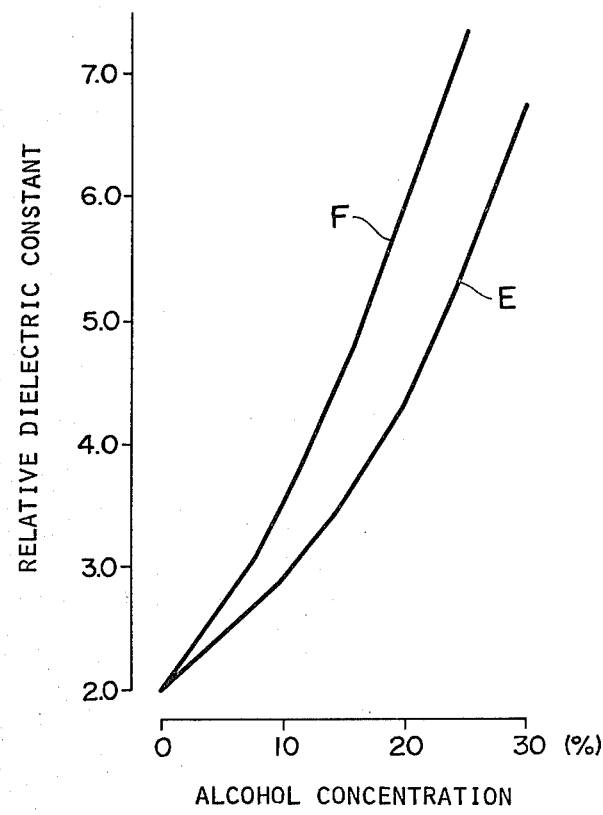
FIG. 9 is a graph of the relation between the relative dielectric constant of fuel and the alcohol concentration in the fuel in the case of gasohol containing methanol or ethanol.

The relation between the alcohol concentration and the relative dielectric constant of gasohol containing methanol or ethanol is shown in FIG. 9, where the line E is the relation in the case of ethanol gasohol and the line F is that in the case of methanol gasohol.

It should be noted that this embodiment has an oscillator, a period detector, and a display, identical with those of the previously-mentioned first embodiment, to measure the period of the oscillatory signal of the oscillator in order to determine the capacitance of the capacitor 70, although they are not depicted.

In order to minimize the influence of the water content in gasohol on the measured capacitance of the capacitor 70, the frequency of the oscillatory signal of the oscillator is set higher than a reference value of 150 KHz in view of the experimental results shown in FIG. 4, because practically-usable gasohol for fuel contains up to 30%-alcohol.

It should be understood that further modifications and variations may be made in the present invention without departing from the spirit and scope of the present invention as set forth in the appended claims.

What is claimed is:

1. An apparatus for determining the level of liquid containing gasoline and alcohol, the alcohol concentration in the liquid having a known value, the apparatus comprising:
   (a) a capacitor partially immersed in the liquid in such a manner that the liquid may enter the capacitor, whereby the capacitance of the capacitor varies with the level of the liquid;
   (b) an oscillator connected to the capacitor for generating an oscillatory signal having a minimum predetermined frequency, the generated frequency increasing in response to the capacitance of the capacitor varying as the level of the fluid decreases from a maximum value, the minimum predetermined frequency of the oscillatory signal of the oscillator depending on the kind of alcohol in the liquid, and being 3 KHz for liquid containing 10%-ethanol; and
   (c) a detector connected to the oscillator for measuring the capacitance of the capacitor according to the frequency of the oscillatory signal of the oscillator to determine the level of the liquid.

2. An apparatus for determining the level of liquid containing gasoline and alcohol, the alcohol concentration in the liquid having a known value, the apparatus comprising:
   (a) a capacitor partially immersed in the liquid in such a manner that the liquid may enter the capacitor, whereby the capacitance of the capacitor varies with the level of the liquid;

(b) an oscillator connected to the capacitor for generating an oscillatory signal having a minimum predetermined frequency, the generated frequency increasing in responsse to the capacitance of the capacitor varying as the level of the fluid decreases from a maximum value, the minimum predetermined frequency of the oscillatory signal of the oscillator depending on the kind of alcohol in the liquid, and being 80 KHz for liquid containing 30%-ethanol; and (c) a detector connected to the oscillator for measuring the capacitance of the capacitor according to the frequency of the oscillatory signal of the oscillator to determine the level of the liquid.

3. An apparatus for determining the level of liquid containing gasoline and alcohol, the alcohol concentration in the liquid having a known value, the apparatus comprising:

(a) a capacitor partially immersed in the liquid in such a manner that the liquid may enter the capacitor, whereby the capacitance of the capacitor varies with the level of the liquid;

(b) an oscillator connected to the capacitor for generating an oscillatory signal having a minimum predetermined frequency, the generated frequency increasing in response to the capacitance of the capacitor varying as the level of the fluid decreases from a maximum value, the minimum predetermined frequency of the oscillatory signal of the oscillator depending on the kind of alcohol in the liquid, and being 15 KHz for liquid containing 10%-methanol; and (c) a detector connected to the oscillator for measuring the capacitance of the capacitor according to the frequency of the oscillatory signal of the oscillator to determine the level of the liquid.

4. An apparatus for determining the level of liquid containing gasoline and alcohol, the alcohol concentration in the liquid having a known value, the apparatus comprising:

(a) a capacitor partially immersed in the liquid in such a manner that the liquid may enter the capacitor, whereby the capacitance of the capacitor varies with the level of the liquid;

(b) an oscillator connected to the capacitor for generating an oscillatory signal having a minimum predetermined frequency, the generated frequency increasing in response to the capacitance of the capacitor varying as the level of the fluid decreases from a maximum value, the minimum predetermined frequency of the oscillatory signal of the oscillator depending on the kind of alcohol in the liquid, and being 150 KHz for liquid containing 30%-methanol; and (c) a detector connected to the oscillator for measuring the capacitance of the capacitor according to the frequency of the oscillatory signal of the oscillator to determine the level of the liquid.

5. A method of enabling determinations to be made of the liquid level of gasohol, i.e., a liquid containing gasoline and alcohol, and susceptible to containing a relatively small percentage of water, the determinations being made with a capacitor immersed in the liquid so that the capacitance of the capacitor varies as the liquid level varies, the capacitor being connected in an oscillator circuit so that changes in the capacitance of the capacitor change the frequency of the oscillator, whereby the oscillator frequency increases as the level decreases from a maximum level, comprising the step of setting the oscillator circuit frequency to a minimum value dependent on the concentration of alcohol in the liquid and such that the capacitance of the capacitor varies independently of the amount of water in the liquid as the liquid level changes.

6. The method of claim 5 further including detecting the frequency derived by the oscillator circuit to indicate the liquid level.

7. The method of claim 5 wherein the minimum value for the frequency is set to higher values as the alcohol concentration in the liquid increases.

* * * * *